United States Patent
Esposito et al.

(10) Patent No.: US 6,495,160 B2
(45) Date of Patent: *Dec. 17, 2002

(54) BIPHASIC MULTICOMPONENT PHARMACEUTICAL DOSAGE FORMS CONTAINING SUBSTANCES ABLE TO MODIFY THE PARTITIONING OF DRUGS

(75) Inventors: Pierandrea Esposito, Ivrea (IT); Nicoletta Coceani, Cividale (IT); Maria Dorly Del Curto, Corvino S.Q. (IT); Fabio Carli, Trieste (IT)

(73) Assignee: Eurand International S.p.A. (IT)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/214,813
(22) PCT Filed: May 13, 1998
(86) PCT No.: PCT/EP98/02846
  § 371 (c)(1),
  (2), (4) Date: Oct. 1, 1999
(87) PCT Pub. No.: WO98/51280
  PCT Pub. Date: Nov. 19, 1998

(65) Prior Publication Data
US 2002/0034539 A1 Mar. 21, 2002

(30) Foreign Application Priority Data
May 13, 1997 (IT) .......................... MI97A1115

(51) Int. Cl.[7] .............. A61K 9/70; A61K 9/48; A61K 9/64; A61K 9/54
(52) U.S. Cl. .............. 424/451; 424/449; 424/450; 424/456; 424/458
(58) Field of Search .................. 424/443, 449, 424/450, 451, 455, 456, 458

(56) References Cited

U.S. PATENT DOCUMENTS

| | | | | |
|---|---|---|---|---|
| 4,719,239 A | * | 1/1988 | Muller et al. | 514/785 |
| 5,407,810 A | * | 4/1995 | Builder et al. | 435/69.1 |
| 5,456,745 A | * | 10/1995 | Roreger et al. | 106/128 |
| 5,747,058 A | * | 5/1998 | Tipton et al. | 424/423 |
| 5,932,755 A | * | 8/1999 | Hashizume et al. | 554/227 |

* cited by examiner

Primary Examiner—Thurman K. Page
Assistant Examiner—S. Tran
(74) Attorney, Agent, or Firm—Thompson Hine LLP

(57) ABSTRACT

The invention provides a biphasic multicomponent pharmaceutical composition consisting of an oil phase and a water phase, comprising one or more lipophilic or oil carrier, one or more hydrophilic or aqueous carrier, one or more ionic or nonionic type surfactant, one or more cosurfactant, one or more active principle for pharmaceutical use, and a compound able to modify the partition of the active principle between said phases selected from the group consisting of N- methyl pyrrolidone (NMP), isopropyl alcohol, propylene glycol, ethoxy-di-glycol, β-cyclodextrin, hydroxypropyl β-cyclodextrin and dimethyl β-cyclodextrin. The invention also provides a method for making the composition.

8 Claims, 11 Drawing Sheets

BIPHASIC MULTICOMPONENT PHARMACEUTICAL DOSAGE FORMS CONTAINING SUBSTANCES ABLE TO MODIFY THE PARTITIONING OF DRUGS

BACKGROUND

This application is a 371 of PCT/98/02846 filed May. 13, 1998.

The possibility to improve the permeation of drugs through the biolocical barrieres such as mucosa or skin, to make the drugs coming into the blood circulation, has been always studied by the pharmaceutical researchers.

Specifically the administration of drugs for systemic absorption through the skin presents some basic advantages, e.g. over the oral route. Among these, the scarce variability of the systemic absorption basically determined by the skin permeation of the drug, which avoids some critical factors of the oral absorption, such as gastric acidity, intestinal motility, presence and quality of food, metabolic demolition of the drug by the liver.

Moreover the transdermic administration of drugs is particularly well suited for long term continous treatments and to avoid side effects related to some drugs. To achieve these goals many different inventions have been prosed based on different technological and scientific approaches.

For example biphasic multicomponent systems such as microemulsions have been proposed; microemulsions can be defined as "optically transparent and thermodynamically stable mixtures, containing two non-mixable components, such as water and oil" ( Schulman, J. H., Stoeckenius W., Prince L. M., Journal of Physical Chemistry, 63, 1677, 1959 ). To obtain such microemulsions four components must be used: 1) dispersed or internal phase; 2) dispersing or external phase; 3) surfactant and 4) cosurfactant, mixed together in molar ratios defined through psudo-ternary plots (Schwuger M., Stickdorn K., Chemical Rewies, 95, 849–864, 1995.

In some specific cases the components can be less than three, more often above four. There can be "oil in water" or "water in oil" microemulsions; Usually oil means lipophilic liquids which cannot be mixed with water, such as organic solvents, oils, fatty acids, whereas water means polar and hydrophilic liquids which can be mixed with water.

B. W. Muller describes, in U.S. Pat. No. 4,719,239 , a multicomponent system, liquid and transparent, for pharmaceutical use, aimed for percutaneous, peoral and transmucosal absorption. In such a system the drug is solubilized either in the oil or water phase, in presence of physiologically acceptable surfactants and cosurfactants, and wherein in certain condition the cosurfactant can assume the function of the oil, or the last can act as surfactant.

The above mentioned patent claims for improvement of percutaneous absorption, compared to other multicomponent systems.

Swiss Pat. Appl. 81-CH0002327 Sandoz based on invention so called microemulsion, claims the obtention of a prolonged percutaneous administration (3 days ) thanks to a reservoir effect.

Eur. Pat. Application 135171 A (Hoffmann-Laroche) claims similarly to U.S. Pat. No. 4,719,239 a pharmaceutical carrier called "pseudo-monophase", consisting of a surfactant (HPL 12–15) soluble in both oil and water phases, with percentages in the range of 5–45%. Such carrier, able to originate percutaneous administration of interferon, can be defined as an oil-water microemulsion and shows an improved diffusion through the skin.

The topical administration for systemic use (via transdermal) of ionic drugs can benefit from biphasic compositions of different kinds, among which the above described microemulsions.

Swiss Patent Appl. CH-86-2597/86 8 (Ciba -Geigy), describes in general, some compositions (such us cream, ointment and gel) which however do not include microemulsions, in particular refers to the anionic drug Diclofenac or its salts (sodic, potassium salt, diethylammonium salt). This patent claims for pharmaceutical compositions comprising Diclofenac or its salt for pharmaceutical use, a percutaneous asorption promoter, of defined chemical formula (ammide tri-substituted), liquid paraffin at body temperature and suitable pharmaceutical excipient.

An important limit to these biphasical compositions called "microemulsions" is represented by the necessity of formulating the composition according to definite percentages rate of component substances, as shown from diagrams of pseudo-ternary phase. This relative composition, that allows the forming of the liquid system, anisotropic and transparent, defined as "microemulsion", is essentially not modifiable because the addition or the substraction of one of the four components (I–IV) out of the component concentration limits will alterate the system, with separation of phases and destruction of the system itself, while substitution of one of the components will originate a system with different characteristics. As consequence, absorption or transdermal permeation of an active principle, released from microemulsion, depends on the composition of the system itself: the dissolved drug will partition itself into the two phases, oil (lipophilic) and water (hydrophilic), in relation to its coefficient of oil/water partitioning. Permeation rate and absorption of drug is therefore determined by the composition and the possibility of modifying such a rate without changing completely the composition of the microemulsion results virtually not realizable.

SUMMARY

The present invention refers to a drug multicomponent biphasical composition that enables to solve the problems of prior art. In particular the present invention refers to a drug composition consisting of an oil phase and a water phase, comprising typically four essential components, defined as (I) dispersed or internal phase, (II) dispersing or external phase, (III) surfactant and (IV) cosurfactant, mixed together in molar ratios determined by the pseudo-ternary phase diagrams and moreover containing a drug (V) and characterized in that it furtherly comprises one compound (VI) able to modify the partitioning coefficient of the drug between oil and water phase, consequently influencing the rate of permeation through the skin. Furthermore the compound (VI) can, in some unexpected cases, form specific complexes with the drug modifying its concentration in the phases of the biphasic system and directly influencing transdermal permeation of the drug itself.

DETAILED DESCRIPTION OF INVENTION

Figure 1:
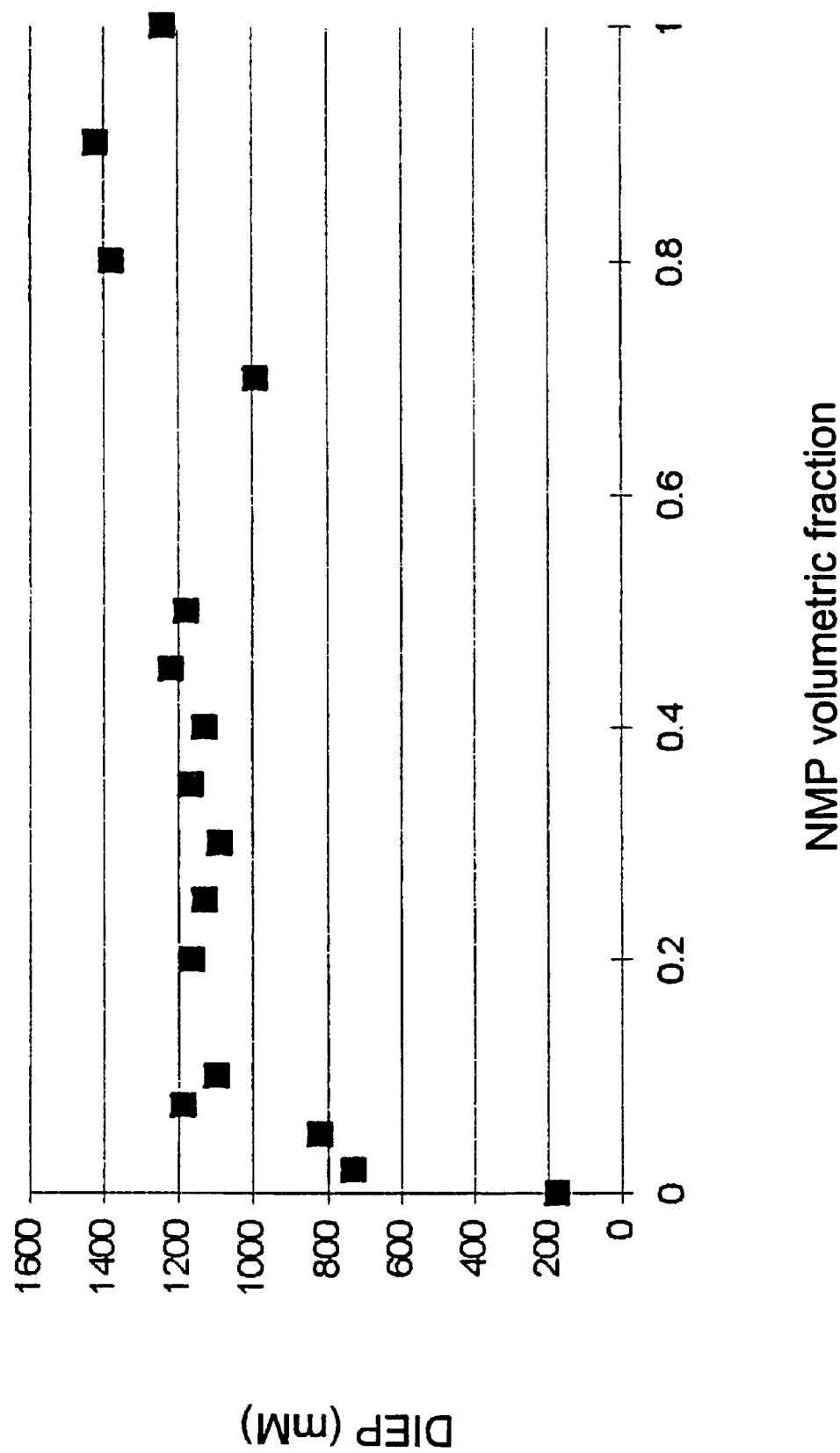
FIG. 1 represents the phase diagram in aqueous solution of the salt of hydroxyethyl pyrrolidine of diclofenac (DIEP) and N-methyl pyrrolidone (NMP).

The invention refers to a pharmaceutical composition mainly, but not only, applicable to topical and systemic administration of drugs by transdermal route. The composition allows improvement in both skin layer absorption and transdermal permeation of ionic and non-ionic drugs. The present invention describes a multicomponent biphasic composition comprising typically four essential components, defined as (I) dispersed or internal phase, (II) dispersing or external phase, (III) surfactant and (IV) cosurfactant, mixed together in molar ratios determined by the pseudo-ternary phase diagrams and moreover containing a drug (V) and a compound (VI), generally but not necessarily of amphyfilic and non-ionic type, able to modify the drug partition coefficient between oil phase and water phase and consequently rate of transdermal permeation of the drug itself. Furthermore the compound (VI) can, in some unexpected cases, form specific complexes with the drug modifying its concentration in biphasic system phases and directly influencing transdermal permeation of the drug itself.

In some specific cases the components can be three because the component (I) or (II) can also act as cosurfactant (IV); more often they are more than four. In some cases, herebelow described, it has been surprisingly found that the same drug (V) can contribute to form the composition taking the place of the surfactant (III) or the cosurfactant (IV). Both internal phase and external phase can be defined as "oil phase" and "aqueous phase", generating multicomponent systems "oil in water" or "water in oil". Generally oil phase is made of lipofilic liquids unable to mix with water as organic solvents, oils and fats, whereas water phase is made up by polar liquids, hydrofilic and normally mixable with water.

An important advantage of the invention is the possibility to improve transdermal permeation of active principles both hydrosoluble (for example diclofenac salts) and lipofilic and scarcely soluble in water (for example papaverine and progesterone) thanks to the possibility to modify the partitioning of the active principle itself between the oil and water phases thanks to the presence of compounds (VI) that modify the partitioning coefficient.

The biphasic multicomponent composition according to the invention includes:

1) one or more lipophylic or oil carriers, called "oil phase", phyisiologically and pharmaceutically acceptable;
2) one or more hydrofilic or water carriers, called "water phase", physiologically and pharmaceutically acceptable;
3) one or more surface agents, called surfactant (III), of ionic or non-ionic type;
4) one component called "cosurfactant" (IV), preferably but not necessarily chosen among alcohols or short aliphatic chain acids;
5) an active principle for pharmaceutical use (V), in enough quantity or concentration for the therapeutic effect desired;
6) one component, preferably but non necessarily amphyfilic (VI), called "partition modifier", able to modify active principle partitioning between oil phase and water phase.

Pharmaceutical active principles (V) that can benefit from the invention are the one used for long-term treatments, like for example non-steroidal anti-inflammatories (NSAID), estrogen or progestins, cardiovasculars, antiviral, antimicotic, antitumoral hormons. Because of the peculiarity of the invention, usable active principles can be relatively hydrosoluble (for example diclofenac salts) or liposoluble (for example estradiol, progesterone), or also scarcely soluble in both carriers (for example acyclovir).

Among drugs that can be formulated according to the invention, can be mentioned as non-limiting examples:

Analgesic and non-steroidal anti-inammatories and their salts: diclofenac sodium, hydroxyethyl pyrrolidine diclofenac, diethylammine diclofenac, ibuprofen, flurbiprofen, ketoprofen, idometacina, mefenamic acid, naproxene, nimesulide, piroxicam.

Antiarithmics: amiodarone, diisopyramide, verapamil, propranolol.

Antibacterials: amoxicillin, flucloxacillin, gentamicin, rifampicin, erythromicine, cephalosporin.

Antimicotic: amfotericin, buconazol nitrate, ketoconazol, econazol, fluconazolo, flucitosina, griseofulvine. itraconazol, miconazol, rystatin, sulconazol, tioconazol.

Antivirals: acyclovir, gancyclovir, AZT, proteasi inhibitor.

Anti-Hypertensives: amlodipine, clonidine, diltiazem, felodipine, guanabenz acetate, isradipine, minoxidil, chloride nicardipine, nifedipine, chloride prazosin, papaverine.

Antidepressives: carbamazepine.

Antihistaminic: difenidramine, chlorfeniramine, chlorciclizine, prometazin, acrivastine, loratadine, terfenadine.

Antitumoral and immunogenic: cyclosporine, decarbazine, etoposide, lomustine, melphalan, mitomicin, mitoanthrone, procarbazine, taxol and derivatives.

Antianxiety, sedative, hypnotic: alprazolam, bromazepam, diazepam, lorazepam, oxazepam, temazepam, sulpiride, triazolam.

β-Blockers: alprenolol, atenolol, oxprenolol, pindolol, propranolol.

β-Agonists: salbutamol, salmeterol.

Cardiac inotropics and cardiovascolars: amrinone, digitoxinn, digoxin, lanatoside C, medigoxine, ubidecarenone.

Corticosteroids: bechlomethasone, betamethasone, budesonide, cortisone acetate, desossimetasone, dexamethasone, fludrocortidone acetate, flunisolide, hydrocortisone, methylprednisolone, prednisone, triamicinolone.

Gastrointestinals and anti $H_2$-histaminics: cimetidine, cisapride, domperidone, famotidine, loperamide, mesalazine, omeprazol, ondansetron, ranitidine chloride.

Hypolipemics: bezafibrate, chlorofibrate, gemfibrozil, probucol.

Anti-Angina: amil nitrate, gliceryltrinitrate, isosorbide dinitrate and mononitrate, pentaeritritol tetranitrate.

Central Action Drugs: for example Nicotina.

Vitamins and nutritional agents: betacarothene, vitamin A, vitamin $B_2$, vitamin D, vitamin E, vitamin K.

Analgesic Opioids: codeine, destropropoxifene, dihydrocodeine, morphine, pentazocine, metadone.

Sexual hormons: danazol, ethynilestradiol, medroxyiprogesterone acetato, methyltestosterone, testosterone, noretistrone, norgestrel, estradiolo, estriolo, progesterone, stilbestrolo, diethylstilbestrol.

Peptidic molecules with different activity: for example LH-RH analogous, calcitonine, glutathione.

Molecules with specific topical activity: for example sun protectants (UV absorbent) skin nourishing, glycolic acid.

Active principles that can particolarly benefit from the invention are for example non-steroidal anti-inflammatories (diclofenac, diclofenac sodium, diclofenac hydroxyethyl pyrrolidine, nimesulide), steroids (progesterone, estradiol, medroxyprogesterone acetate), different cardiovasculars (nifedipine, papaverine, diltiazem, verapamil), antivirals (acyclovir), antimicotic (ketoconazol, itraconazol). As oil carriers according to the invention can be mentioned both natural products and synthetic or semsynthetic products called "oils" because not mixable or only partially mixable with water. All components can be used alone or, if possible, in mixtures with different percentages. Among the oil components which can be used as dispersed phase (I), but also as dispersing phase (II):

1) saturated and unsaturated natural oils: olive oil, peanuts, soy, mais, coconut, palm, sesame oil and similars.
2) mono-, di- e triglycerids, semisynthetic and synthetic: containing saturated and/or unsaturated fatty acids (with aliphatic chains length variable between $C_6$ and $C_{22}$), their poly-hydroxyethyl derivatives. For example: capricocaprylic triglycerids, (Mygliol™, Captex™, Labrafac™ Lipo), polihydroxylated triglycerids of different kind, saturated or unsaturated (Labrafil™, Labrafac™ Hydro, Gelucire™).
3) "liquid waxes": isopropyl miristate, isopropyl-caprinate, -caprilate, -laurate, -palmitate, -stearate; fatty acid esters, such as ethyl oleate, oleyl oleate.
4) aliphatic and aromatic alcohols: hexadecyl alcohol, oleic alcohol, lauric alcohol, cetylstearyl alcohol, benzyl alcohol and their poly-hydroxyethylated derivatives.
5) aliphatic carboxylic acids: preferably with short or middle ($C_4$–$C_{10}$) chain, like is decanoic acid, butanoic acid, etc., and their poly-hydroxyethyl derivatives.
6) silicon oils For example, a preferred composition according to the invention can contain, as oily dispersed phase (I) a mixture of Labrafac™ Hydro (PEG 4 glyceryl caprilate-caprate) and benzyl alcohol, witb relative ratios between 100 and 0,01.

Examples of hydrophylic carriers according to the invention are natural products, synthetic or semi-synthetic products, which can be defined as aqueous carriers not mixable or only partially mixable with oil. All components can be used alone or if possible in mixtures with different percentages. Among aqueous components which can be used preferably as dispersing phase (II), but also as dispersed phase (I), we can mention:

1) water, as such, or buffered at different pH and ionic force.
2) aqueous solutions of hydrophilic polymers which are hydrosoluble or hydrodispersable of various nature, like polyethylenglycol, polyvinylpyrrolidone, polyacrylic acids and derivatives (for example Carbopol™, Premulen™, ecc.), polymethacrylic acids and derivatives (for example Eudragit™), polyoxyethylene-polyoxypropilene copolymers (for example Poloxamer, Lutrol™), polysaccharides of various nature, for example dextran, xanthan, scleroglucan, arabic gum, guar gum, chitosan, cellulose and starch derivatives.
3) mono- or polyhydroxyl aliphatic alcohols, preferably of short chain ($C_2$–$C_4$).
4) polyethylenglycols (for example PEG 200, PEG 400, PEG 600, PEG 1000)
5) polyglycolic glycerides (for example Labrasol™).
6) polyglycols, like for example propylene glycol, tetraglycol, ethoxydiglycol (Transcutol™).

For example, a preferred composition according to the invention can include as dispersing aqueous phase (II) a solution of Lutrol™ 127 in water, at a concentrations in the range. 1% and 50%.

The presence of surfactant (III) and cosurfactant (IV) in different ratios depending on the nature and type of the components is of paramount relevance in order to form the biphasic system in accordance to the invention.

Among the surfactants (III) we can mention all non- ionic surfactants with HLB value higher than 7, like for example: sorbitane esters of fatty acids (Tween, Capmul™, Liposorb™), polypropylenoxide-polyethyleneoxide copolymers (Poloxamer), polyethyleneglycol esters (PEG-glycerol, Labrasol, Labrafil with HLB 6–7), PEG esters and long-chain aliphatic acids or alcohols (Cremophor), polyglyceryl esters (Plurol), esters of saccharides and fatty acids (sucroesters). If necessary also anionic surfactants can be used (e.g., sodium laurylsulphate, sodium stearate, sodium oleate ) or cationic ( e.g., tricetol ), as well as lecithins, phospholipids and their semi-synthetic or synthetic derivatives.

Among the cosurfactants (IV) we mention short-chain alcohols, e.g. ethanol, 2-propanol, n-butanol, isopropanol; aliphatic acids (e.g. butirric acid, valerianic, capronic acid) with short or middle chain length; aromatic alcohols such as benzyl alcohol. Middle-chain aliphatic alcohols and acids ($C_8$–$C_{12}$), such as decanoic acid, lauric acid, caprinyl alcohol, lauryl alcohol. Further examples of cosurfactants are esters or ethers of aliphatic, middle-long-chain acids or alcohols with mono or polyhydroxyl alcohols.

Some of the mentioned cosurfactants can be at the same time constituents of the oily phase of the microemulsion.

For example a preferred composition according to the invention includes: as an oily dispersed internal phase (I), a mixture of Labrafac Hydro (PEG-4 glyceryl capylate-caprate) and benzyl alcohol, at ratios comprised in the range 10:1 to 1:1, as an aqueous dispersing phase (II) a Lutrol 127 solution in water, with concentrations in the range 1%–50%, and a surfactant (III), Tween 80, in the concentration range comprised between 5% –15% by volume. In this composition one of the components of the phase (I) (benzyl alcohol) acts also as cosurfactant (IV).

Essential components of this invention are the compounds (VI), which are able to modify unexpectedly the oil/water partition coefficient of the drug in the system. Usually compounds (VI) are generally, though not necessarily, amphiphylic and non-ionic. The modification of the partition of the drug depends on the type and concentration of compound (VI): consequently the active principle may enrich either phase, with consequent influx on the percutaneous absorption rate. This result can be obtained without changing the composition according to the invention in its constituents (I–V). As partitioning modifiers we can mention: N-methyl pyrrolidone (NMP), isopropyl alcohol, propylene glycol, ethoxydiglycol, propylene glycol dipelargonate (DPPG), betacylodextrin, hydroxypropyl beta-cyclodextrin, and dimethyl beta-cyclodextrin.

Furthermore some compounds (VI) (NMP and cyclodextrins) can form specific complexes with some drugs, directly affecting the concentration in the phases of the biphasic system, and the transdermal permeation of the drugs.

Among the compounds (VI) N-methyl-pyrrolidone is particularly interesting; for example a preferred composition according to the invention includes: Labrafac Hydro (PEG-4 glyceryl caprylate-caprate) and benzyl alcohol with relative ratios within the range 10:1–1:1 (and with concentration comprised between 5% and 15% v/v); water (from 45% to 60% in volume ), Lutrol 127 (5–15%),Tween 80, in a percentage between 5 and 20% by volume, and NMP in volumetric concentrations in the range 3% –20%.

The composition of the invention can typically include:
1. One or more lipophilic or oily carriers with percentages in the range 0,5% –80%, preferably 5%–40% by weight.
2. One or more aqueous components, in the weight range of 0.5% –75%, preferably 35%–70% by weight.
3. Surfactants (III) ,ionic or non-ionic, in the range 0.1%–50% , preferably 1%–20%.
4. Cosurfactants (IV) in the range 0%–60%, preferably 0%–20%.
5. A specific surfactant/cosurfactant ratio$\geq$1.
6. One or more drugs preferably in the range 0.1%–60%, if dissolved in the system; 0.1%–25% if the drug is dispersed.
7. One compound ("partition modifier") (VI), in the range 0.1%–25%,preferably 2.5%–25% by weight.

The invention can also include all the common pharmaceutical excipients such as flavours, preservatives, dyes. Furthermore compositions of the invention can contain suspending agents, gelling agents, viscosity enhancers. For example, colloidal gelling agents such as silica gels (Aerosil®) in the concentration range 1%–15%, preferably 3%–10%. Also polymeric gelling agents can be used: examples are the polyacrylic acid derivatives (Carbopol, Noveon, Pemulen) polymethacrylate (Eudragit®), both in the range 0.1–10%; polyethylene oxide-polypropylene oxide copolymers (e.g. Lutrol®), usually between 2.5% and 30%; polyvinilpyrrolidone (e.g. Plasdone®, Kollidon®), cellulose derivatives like hydroxypropylcellulose, hydroxypropylmethylcellulose (Methocel®), sodium carboxymethylcellulose; polysaccharides like xanthan (Satiaxane®), scleroglucan (Actigum®),guar gum, arabic gum, locust bean gum. Usually these substances are in the range 0.1 and 20% in weight.

Generally, any substance capable of forming gels in presence of various amounts of water or other solvents, can be used for the purpose of the invention.

The preparation process is generally performed by initially mixing the lipophilic or oily carrier, the cosurfactant, and a fraction of the surfactant necessary for the formulation, variable between 0% and 75% of the calculated total; this system is kept under mild stirring in a mixer or in an emulsifier. The preparation temperature and the thermal stability range may vary depending on the components; usually the temperature is in the range of 5°–85° C., preferably 15–45° C. The water phase is added to the other components in the reactor, usually at room temperature, under moderate stirring temperature control. Once the two phases are mixed, the remaining part of the surfactant is added, allowing the formation of a clear or semi-transparent multi-component system. If necessary further surfactant and cosurfactant are added; the compound VI "partitioning modifier" is usually added to one of the phases before mixing, depending on its mixability with the aqueous or oily phase.

The quantity and concentration of the drug depends on the therapeutical purpose of the composition; the method of adding the drug depends on its physico-chemical properties. Usually the drug is added to the already formed composition, being soluble in one or both phases of the system; so both hydrophilic (e.g. diclofenac sodium) and lipophilic drugs (e.g. progesterone) can be added to the system. In this case, the solubility of the drug in the composition is advantageously higher than in the single separated phases. Where the drug concentration is lower than its solubility in the phases, it is possible to dissolve it in the aqueous or oily phase before mixing them and forming the system.

Another characteristic of the invention is that the formation of complexes between is compounds (VI) and drugs with surfactant activity (for example hydroxyethyl pyrrolidine diclofenac) can strongly influence the surface properties of the drug and that acts on creation of the oil-water interface in the multicomponent system. Consequently, the preparation of compositions according to the invention requires minor percentages of surfactacts (III), when a drug or a partitioning modifyer-drug complex with surfactant action is present in the above composition. In such cases the drug results to be not only a solute but also an essential component of the composition.

The multicomponents systems of the invention can be further formulated as the pharmaceutical dosage forms known in the art for topical or systemic administration of drugs. For example compositions can be introduced in gel formulations, as above described, using known processes, as the addition of gelling polymers under mixing and vacuum in order to avoid the formation of air bubbles. The gel matrix can be directly applied to the skin or to be included in a transdermal application device such as the Hilltop® chamber. The multicomponent composition can also be included, as liquid, viscous liquid or gel, in a transdermal system, e.g. a reservoir system consisting of a device and a diffusion membrane, and "drug-in-adhesive" system directly on the skin, similarly to known systems (for example Extraderm®, CIBA).

The composition can also be inserted in multilayer transdermal systems of laminate and multilaminate kind, or can directly contain the adhesive material in order to form the transdermal systems known as "drug-in-adhesive".

For transmucosal applications the invention can be formulated in every dosage forms known in the art. For example, composition suitable for topic administration can be formulated in gel directly applicable, compostions for oral or transmucosal use can be formulated in liquid capsule, soft-gel capsules, suppositories and applicators normally used in the administration of aqueous or oil liquids.

Compositions according to the present invention can increase the skin and transdermal permeation rate of the active principles without the necessity of modify the composition of the multicomponent biphasic system in its essential elements (defined as components I–IV). This unexpected characteristic is realizable thanks to the presence in the formulation, in the aqueous and oil phase, of particular compounds, generally but not necessarily of amphiphilic kind, able of modifying the partioning coefficient of the active principle between the oil (lipophilic) and water (hydrophilic) component.

Further unexpected characteristic of the invention is the unexpected interaction between the drug and some of the mentioned amphiphilic compounds, resulting from the formation of specific complexes able of modifying the oil-water partitioning properties and the transdermal permeation of the active principle. Furthermore formation of these specific complexes, in the case of drugs with surface active properties, influences in a dramatic way the water-oil interface properties of the drug in itself and acts of the formation of oil-water interface of the multicomponent system.

Some non limiting examples are given to show the components and the preparation process of some compositions of the invention.

EXAMPLE 1

The preparation according to the present invention of liquid multi-component biphasic compositions is reported for example purpose.

The process of preparation is described in general in the above paragraphs: if not otherwise specified, the method of preparation consists in mixing the oil, the cosurfactant and part of the surfactant; further mixing the water phase containing the component (VI), "partition modifier"; adding the remaining surfactant until the system is transparent and the active principle is dissolved or suspended. In the case of drugs known as having surface activity it is possible, though not absolutely necessary, to invert the steps of adding the drug and the remaining amount of surfactant. The temperature of preparation of the sample is T=25° C., unless otherwise specified.

The comparative data with compositions according to the state of the art are shown in FIGS. 5–9

Composition I

| | |
|---|---|
| Water | 47.93% by weight |
| Benzyl alcohol | 8.2% by weight |
| Labrafac Hydro | 7.91% by weight |
| N-methylpyrrolidone (NMP) | 12.56% by weight |
| Tween 80 | 19.90% by weight |
| Diclofenac hydroxyethyl pyrrolidine (DIEP) | 3.50% by weight |

Composition II
A composition is prepared, corresponding to composition I, where the "partition modifier" NMP accounts for 10.75% by weight, and the water content is increased to 49.74% by weight.
Composition III
A composition is prepared, corresponding to composition I, where the "partition modifier" NMP accounts for 6.25% by weight, and the water content is increased to 52.24% by weight.
Composition IV
A composition is prepared, corresponding to composition 1, where the "partition modifier" NMP accounts for 3.25% by weight, and the water content is increased to 52.24% by weight.
Composition V
A composition is prepared, corresponding to composition III, where the "partition modifier" NMP accounts for 6.25% by weight, and the active principle is sodium diclofenac (3.50% by weight)
Composition VI
A composition is prepared, corresponding to composition V, where the active principle is sodium diclofenac (3.50% by weight), and the "partition modifier" NMP accounts for 3.25% by weight.
Composition VII

| | |
|---|---|
| Water | 49.00% by weight |
| Benzyl alcohol | 8.20% by weight |
| Labrafac Hydro | 8.20% by weight |
| Transcutol | 13.10% by weight |
| Tween 80 | 18.00% by weight |
| Diclofenac hydroxyethyl pyrrolidine | 3.50% by weight |

Composition VIII

| | |
|---|---|
| Water | 49.00% by weight |
| Benzyl alcohol | 7.90% by weight |
| Labrafac Hydro | 7.90% by weight |
| Propylenglycol | 12.70% by weight |
| Tween 80 | 19.00% by weight |
| Diclofenac hydroxyethyl pyrrolidine | 3.50% by weight |

Composition IX
A composition is prepared, corresponding to composition VIII, where the "partition modifier" propylene glycol accounts for 6.35% by weight, and the water content is 52.2% by weight.
Composition X
A composition is prepared, corresponding to composition VIII, where the "partition modifier" propylene glycol accounts for 6.35% by weight, and the water content is 55.35% by weight.
Composition XI
A composition is prepared, corresponding to composition VIII, where the "partition modifier" propylene glycol accounts for 15.85% by weight, and the water content is 45.85% by weight.

Composition XII

| Water | 49.5% by weight |
|---|---|
| Benzyl alcohol | 7.8% by weight |
| Labrafac Hydro | 7.8% by weight |
| NMP | 12.4% by weight |
| Tween 80 | 22.5% by weight |

The active principle papaverine hydrochloride is thus added and dissolved at a concentration of 20 mg/ml of composition.

Composition XIII

A composition is prepared, corresponding to composition XII, where the "partition is modifier" NMP accounts for 12.5% by weight, and the active principle is verapamil hydrochloride, at a concentration of 20 mg/ml.

Composition XIV

| Water | 48.6% by weight |
|---|---|
| Benzyl alcohol | 8.1% by weight |
| Labrafac Hydro | 7.9% by weight |
| NMP | 12.3% by weight |
| Tween 80 | 23.1% by weight |

The active principle nimesulide is thus added and dissolved at a concentration of 3 mg/ml of composition.

Composition XV

A composition is prepared, corresponding to composition XIV, where the "partition modifier" NMP accounts for 12.0% by weight, and the active principle is estradiol at a concentration of 2.5, 5 or 10 mg/ml. The water content is 48.9% by weight.

Composition XVI

The following composition is prepared:

| Water | 35.7% by weight |
|---|---|
| Labrafil CS2125 | 15.0% by weight |
| Lutrol F127 | 12.0% by weight |
| NMP | 12.0% by weight |
| Tween 80 | 19.4% by weight |
| Pemulen TR-1 | 1.0% by weight |
| Acyclovir | 4.9% by weight |

The composition contains a part of the active principle in dissolved form, and another part as a micronised suspension homogenously dispersed within the semi-transparent system, in order to reach 5% by weight. Pemulen TR-1 is added to the composition after dissolving/dispersing the active principle into the other components.

Composition XVII

The following composition is prepared:

| Water | 47.72% by weight |
|---|---|
| Labrafac Hydro | 8.44% by weight |
| Benzyl alcohol | 8.44% by weight |
| NMP | 11.90% by weight |
| Tween 80 | 12.67% by weight |
| Lutrol F127 | 6.78% by weight |
| Triethanolamine | 0.25% by weight |
| Diclofenac hydroxyethyl pyrrolidine | 3.80% by weight |

Composition XVIII

The following composition is prepared:

| Water | 47.72% by weight |
|---|---|
| Labrafil CS 2125 | 12.66% by weight |
| Benzyl alcohol | 4.22% by weight |
| NMP | 11.90% by weight |
| Tween 80 | 12.67% by weight |
| Lutrol F127 | 6.78% by weight |
| Triethanolamine | 0.25% by weight |
| Nifedipine | 3.80% by weight |

EXAMPLE 2

The preparation, according to example 1, of gelled multi-component biphasic compositions is reported for example purpose.

The process of preparation is described in general in the above paragraphs: the method of preparation consists in mixing the oil, the co-surfactant and part of the surfactant; further mixing the water phase containing the component (VI), "partition modifier"; adding the remaining surfactant until the system is transparent and the active principle is dissolved or suspended.

Once the active principle is dissolved, the gelling material is added under stirring to the composition, in order to disperse / dissolve it uniformly into the composition. If necessary, the gelling polymers or colloids may be added in a reactor under vacuum, in order to prevent the formation of air bubbles.

In the case of drugs known as having surface activity it is possible, though not absolutely necessary, to invert the steps of adding the drug and the remaining amount of surfactant. The temperature of preparation of the sample is T=25° C., unless otherwise specified.

Composition XIX

| Water | 42.44% by weight |
|---|---|
| Benzyl alcohol | 6.68% by weight |
| Lubrafac Hydro | 6.68% by weight |
| N-methylpyrrolidone (NMP) | 10.62% by weight |
| Tween 80 | 26.82% by weight |
| Diclofenac hydroxyethyl pyrrolidine (DIEP) | 3.58% by weight |

An amount of polyacrylic acid Carbopol® 940 P is added under stirring and at room temperature to the thus prepared composition, in order to turn the composition into a stable and transparent gel. The percentage of Carbopol 940P was found to be 3.18% by weight.

Composition XX

| Water | 42.43% by weight |
|---|---|
| Benzyl alcohol | 6.68% by weight |
| Lubrafac Hydro | 6.68% by weight |
| N-methylpyrrolidone (NMP) | 10.62% by weight |
| Tween 80 | 26.82% by weight |

-continued

| | |
|---|---|
| Diclofenac hydroxyethyl pyrrolidine | 3.58% by weight |
| Pemulen TR-1 | 3.19% by weight |

A composition corresponding to composition XVII is prepared, where the "partition modifier" NMP accounts for 10.62% by weight, the active principle is DIEP at a concentration of 3.58% by weight, and the gelling agent is Pemulen TR-1 at 3.19%.

Composition XXI

A gelled composition is prepared according to the present invention, being made of:

| | |
|---|---|
| Water | 42.66% by weight |
| Labrafac Hydro | 8.25% by weight |
| Benzyl alcohol | 8.36% by weight |
| NMP | 10.98% by weight |
| Tween 80 | 11.50% by weight |
| Lutrol F127 | 10.50% by weight |
| Triethanolamine | 0.96% by weight |
| DIEP (diclofenac hydroxyethyl pyrrolidine) | 3.52% by weight |
| Carbopol 940P | 3.27% by weight |

The preparation is started by dissolving Lutrol F127 in water, in presence of NMP and triethanolamine, under stirring at 5° C. Thereafter the oil components (Labrafac, benzyl alcohol) and the surfactant are added to the aqueous phase, while the temperature of the reaction vessel is raised to 25° C. The DIEP is dissolved into the transparent system, and the multi-component system is then gelled by adding the gelling polymer Carbopol 940P.

EXAMPLE 3

Composition XXII The following composition is prepared:

| | |
|---|---|
| Water | 48.10% by weight |
| Benzyl alcohol | 8.03% by weight |
| Labrafac Hydro | 7.91% by weight |
| N-methylpyrrolidone (NMP) | 12.56% by weight |
| Tween 80 | 19.90% by weight |
| Diclofenac hydroxyethyl pyrrolidine (DIEP) | 3.50% by weight |

The composition in thus formulated into a transdermal system ("reservoir" type) consisting of a diffusional membrane selected among those commercially available (3M type 10A/AA), and a polymer envelope containing the composition itself.

Composition XXIII

A composition corresponding to composition XIX is prepared, where the "partition modifier" NMP accounts for 10.98% by weight, the active principle is DIEP at a concentration of 3.5% by weight, and the gelled matrix is loaded on a matrix support available on the market (e.g. Hilltop® Chamber), supported by an external adhesive layer.

EXAMPLE 4

Effect of the "partition modifier" on the partition of the active principles among the oil components of the system The apparent partition coefficient ($P_m$) for some active principles, among the oil and water phases of compositions according to the invention, is reported for example purpose. The results show that, in presence of "partition modifiers" according to the present invention (component VI), the active principle is distributed, in a surprising manner, towards one or the other phases of the composition. Measured amounts of the oil component (Labrafac Hydro, Benzyl alcohol 1:1) were contacted, under stirring for 24 hours, with equal volumes of water components (Acqua) containing different percentages of some "partition modifiers" (NMP, propylene glycol-PG, Transcutol-TC, Isopropanol-IPOA). The water volume contained a starting concentration of active principle ($C_0$) which was lower than the solubility of the active principle in each of the two phases. At the end of the experiment, the concentrations of active principle in the water phase ($C_A$) were measured by cromatography (HPLC). The apparent partition coefficient $P_m$ was calculated according to the following formula:

$$P_m = C_{oil}/C_{water} = (C_0 - C_A)/C_A \quad (1)$$

The results are reported in Table 1.

TABLE 1

Table 1: apparent partition coefficient ($P_m$) for some active principles, among the oil and water phases of compositions according to the invention.

| % partition modifier in aqueous phase | | Partition coefficient ($P_m$) of the Active Principle | | |
|---|---|---|---|---|
| | | DIEP | DIC-Na | NIME |
| NMP | 0% | 8.43 | 9.45 | 1.75 |
| NMP | 5% | 2.94 | 4.52 | 36.7 |
| NMP | 10% | 2.07 | 4.49 | 63.5 |
| NMP | 15% | 0.53 | — | 98.3 |
| NMP | 17.5% | 0.62 | — | — |
| NMP | 20% | 0.06 | 2.2 | 29.6 |
| PG | 0% | 8.43 | | |
| PG | 10% | 7.58 | | |
| PG | 15% | 5.96 | | |
| PG | 20% | 4.92 | | |
| PG | 25% | 4.65 | | |
| TC | 0% | 8.43 | | |
| TC | 10% | 2.12 | | |
| TC | 15% | 1.25 | | |
| TC | 20% | 0.27 | | |
| TC | 25% | 0.19 | | |
| IPO | 0% | 8.43 | | |
| IPO | 5% | 10.1 | | |
| IPO | 10% | 9.47 | | |
| IPO | 15% | 12.82 | | |
| IPO | 20% | 11.87 | | |

Oily phase: Labrafac Hydro, benzyl alcohol 1:1
Aqueous phase: Water, partition modifier
DIEP: Diclofenac hydroxyethyl pyrrolidine
DIC-Na: Diclofenac sodium
NIME: Nimesulide
NMP: N-methylpyrrolidone
PG: Propylenglycol
TC: Transcutol
IPO: Isopropyl alcohol

EXAMPLE 5

Specific interaction (complexation) of "partition modifiers" with some active principles, and consequent modification of partition of the active principles among the oil and aqueous components.

It was unexpectedly found that some type (VI) components "partition modifiers" according to the present invention can interact with certain active principles by forming complexes at defined molar ratios.

Therefore such interaction cannot be ascribed to the action of a co-solvent (aspecific interaction), but it is specific and typical for certain couples active principle / "partition modifier". The interaction was determined by the "phase solubility" method (T. Higuchi and A. Connors, in Advances in Analytical Chemistry and Instrumentation, 4, 46, 1965).

Figure 2:
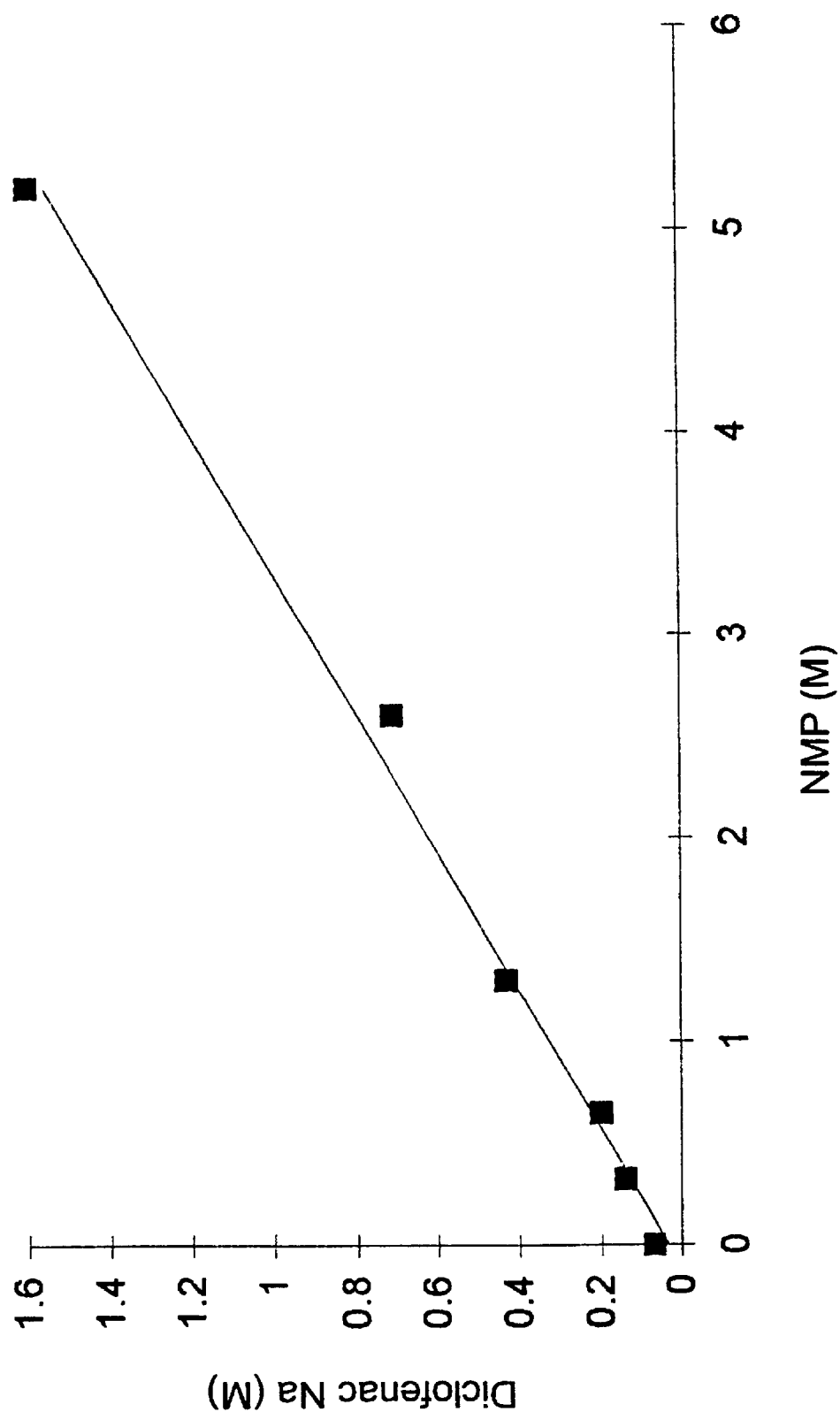
FIG. 2 represents the phase diagram in aqueous solution of the sodium salt of diclofenac and N-methyl pyrrolidone (NMP).
Figure 3:
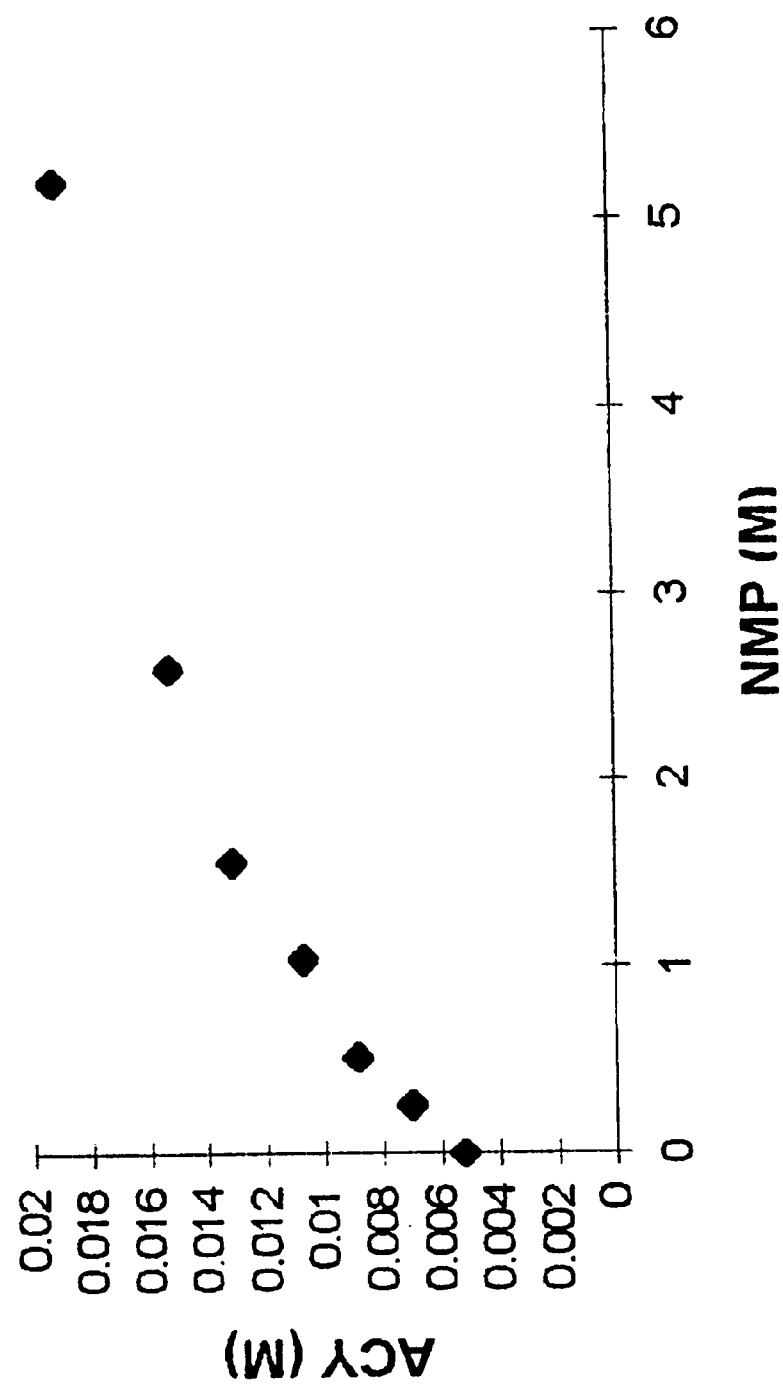
FIG. 3 represents the phase diagram in aqueous solution of acyclovir (ACY) and N-methyl pyrrolidone (NMP).
Figure 4:
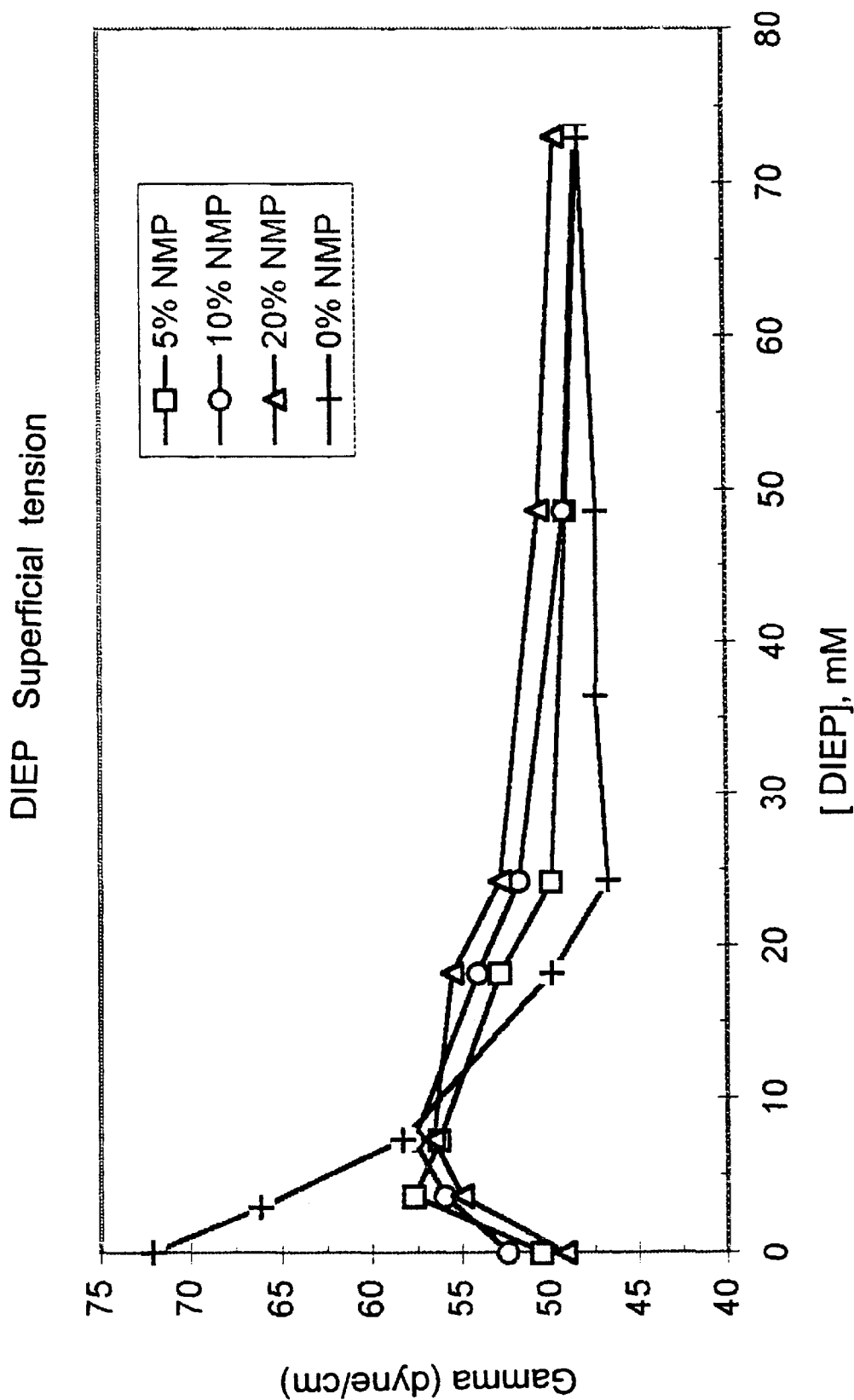
FIG. 4 represents the surface tension of DIEP aqueous solutions in the presence of different concentrations of NMP (% by volume).

Amounts of drug were added to a fixed volume of water and growing percentages of NMP ("partition modifier") in order to obtain a final concentration of drug being always higher than its solubility. At the steady state, samples were extracted from these solutions and analysed by UV spectrophotometry. By plotting the concentration of a component (e.g. the active principle) in function of the quantity of another component (e.g. the "partition modifier", NMP), it was possible to obtain the phase diagram in solution of the various systems drug-NMP. The thus obtained diagram, of the $A_L$ type (T. Higuchi and A. Connors, cited above) shows that the solubility of the active principle grows linearly in function of the NMP concentration, at least within certain ranges of concentration of the complexing agent: this behaviour is indicative of a specific interactions (complexation) between the two components. For example purpose, we report the phase diagrams in aqueous solution of diclofenac hydroxyethylpyrrolidine (DIEP) - N-methylpyrrolidone (NMP) (FIG. 1), sodium diclofenac - NMP (FIG. 2), Acyclovir - NMP (FIG. 3), where FIG. 1 shows the phase diagrams in aqueous solution of diclofenac hydroxyethylpyrrolidine salt (DIEP) and N-methylpyrrolidone;

FIG. 2 shows the phase diagrams in aqueous solution of diclofenac sodium salt and N-methylpyrrolidone (NMP) (the diagram has y=0.293x+0.0327 and $R^2$=0.9931);

FIG. 3 shows the phase diagrams in aqueous solution of acyclovir (ACY) and N-methylpyrrolidone (NMP).

The unexpected formation of complexes may be a co-factor in the modification of partition of active principles among the oil and water phase of the compositions according to the invention.

EXAMPLE 6

Effect of the "partition modifier" and drugs having surface activity on the oil-water interface formation, and consequent stabilisation of the composition itself.

The formation of complexes between the type (VI) component "partition modifier" and drugs having surface activity (e.g. DIEP) modifies the surface properties of the drug itself. This phenomenon influences the formation of the oil/water interface in the multi-component system: consequently, the preparation of compositions according to the invention requires lower amounts of surfactants (III) if the composition contains a drug or a drug-partition modifier complex having surface activity. In this case the drug represents not just a mere solute, but an essential component of the composition.

In order to demonstrate this aspect, we measured the trend of the surface tension (gamma, dyne/ cm) of water solutions of DIEP, in function of the drug concentration, and at different concentrations of NMP (% volume).

The unexpected influx of the drug on the interface formation and consequently on the formation of the compositions of the invention is shown in table 2. It can be seen that, being the other components unchanged, the stabilising action of DIEP allows to decrease the concentration of surfactant (Tween 80) necessary to form the multi-component system.

TABLE 2

| Composition | $H_2O$ (%) | NMP (%) | Labrafac Hydro | Benzyl alcohol (%) | Tween 80 (%) | DIEP (%) |
|---|---|---|---|---|---|---|
| XXIV | 49.16 | 12.66 | 7.97 | 8.09 | 22.12 | 0 |
| XXV | 49.03 | 12.63 | 7.95 | 8.07 | 22.06 | .026 |
| XXVI | 48.80 | 12.56 | 7.91 | 8.03 | 21.95 | 0.75 |
| XXVII | 48.70 | 12.53 | 7.89 | 8.00 | 21.90 | 1.02 |
| XXVII | 46.09 | 12.07 | 7.48 | 7.59 | 20.23 | 3.37 |

EXAMPLE 7

Comparative compositions according to the state of the art.

The preparation of some multi-component systems according to the state of the art is reported for example purpose. The process of preparation is known from the prior art: if not otherwise specified, the method of preparation consists in mixing the oil, the co-surfactant, the surfactant, the water phase; adding the remaining surfactant until transparency of the system; dissolving or suspending the active principle; optionally adding further components (e.g. gelling agents). In order to allow direct comparison of the compositions according to the invention and to the prior art, compositions containing the same excipients were prepared, only differing in the presence (or absence) of the "partition modifiers". The comparative data are reported in FIGS. 5–9. Comparative composition A (compared with composition I, example 1)

| | |
|---|---|
| Water | 60.70% by weight |
| Benzyl alcohol | 8.00% by weight |
| Labrafac Hydro | 7.90% by weight |
| Tween 80 | 19.90% by weight |
| Diclofenac hydroxyethyl pyrrolidine (DIEP) | 3.50% by weight |

Comparative composition B (compared with composition V, example 1)

| | |
|---|---|
| Water | 60.70% by weight |
| Benzyl alcohol | 8.00% by weight |
| Labrafac Hydro | 7.90% by weight |
| Tween 80 | 19.90% by weight |
| Diclofenac Sodium | 3.50% by weight |

Comparative composition C (compared with composition XII, example 1)

| | |
|---|---|
| Water | 49.7% by weight |
| Benzyl alcohol | 7.8% by weight |
| Labrafac Hydro | 7.8% by weight |
| NMP | 12.4% by weight |
| Tween 80 | 22.3% by weight |
| Papaverine hydrochloride | 20 mg/mL of formulation |

Comparative composition D (compared with composition XIV, example 1)

| | |
|---|---|
| Water | 60.9% by weight |
| Benzyl alcohol | 8.1% by weight |
| Labrafac Hydro | 7.9% by weight |

-continued

| | |
|---|---|
| Tween 80 | 23.1% by weight |
| Nimesulide | 3 mg/mL of formulation |

Comparative composition E (compared with composition XVI, example 1)

| | |
|---|---|
| Water | 47.7% by weight |
| Labrafil CS2125 | 15.0% by weight |
| Lutrol F127 | 12.0% by weight |
| Tween 80 | 19.4% by weight |
| Pemulen TR-1 | 1.0% by weight |
| Acyclovir | 4.9% by weight |

EXAMPLE 8

Cynetic of transdermal permeation of active principles formulated according to the invention, and comparison with the state of the art.

In-vitro transdermal permeation assays were performed on whole fresh cutis taken from eutimic naked rats, using a diffusion cell apparatus (Franz cells). The method generally described in Y. W. Chien, *Transdermal Controlled Systemic Medications; Marcel Dekker, NYC and Basel* (1987) was applied. The compositions according to the invention and the reference compositions were introduced in the donor compartment of the Franz cells, at constant and defined volumes/ amounts (generally 2.5–3 ml, or 2.5–3 g). The acceptor compartment contained saline solution and phosphate buffer, pH 7.4; the skin samples were interposed between the two compartments, and the temperature was kept constant at 37° C. for the whole duration of the experiment. At defined times, samples were taken from the acceptor phases, and the content was analysed by chromatograpy (HPLC). The results were reported as transdermal permeation curves, whose linear tract allowed to extrapolate the flux values or transdermal permeation rate, to be defined as:

$$J = dQ/dt \quad (2)$$

where Q stands for the amount of permeated drug per surface unit ($cm^2$), and t is the time expressed in hours.

We report the results obtained by the compositions according to the invention, containing some of the active principles and "partition modifiers" as mentioned above; we also report their comparison with the reference compositions. These unexpected results are referred to: (a) diclofenac hydroxyethyl pyrrolidine (DIEP), composition I (FIG. 5); sodium diclofenac, composition V (FIG. 6); papaverine hydrochloride, composition XII (FIG. 7); nimesulide, composition XIV (FIG. 8); acyclovir, composition XIV (FIG. 9).

Figure 5:
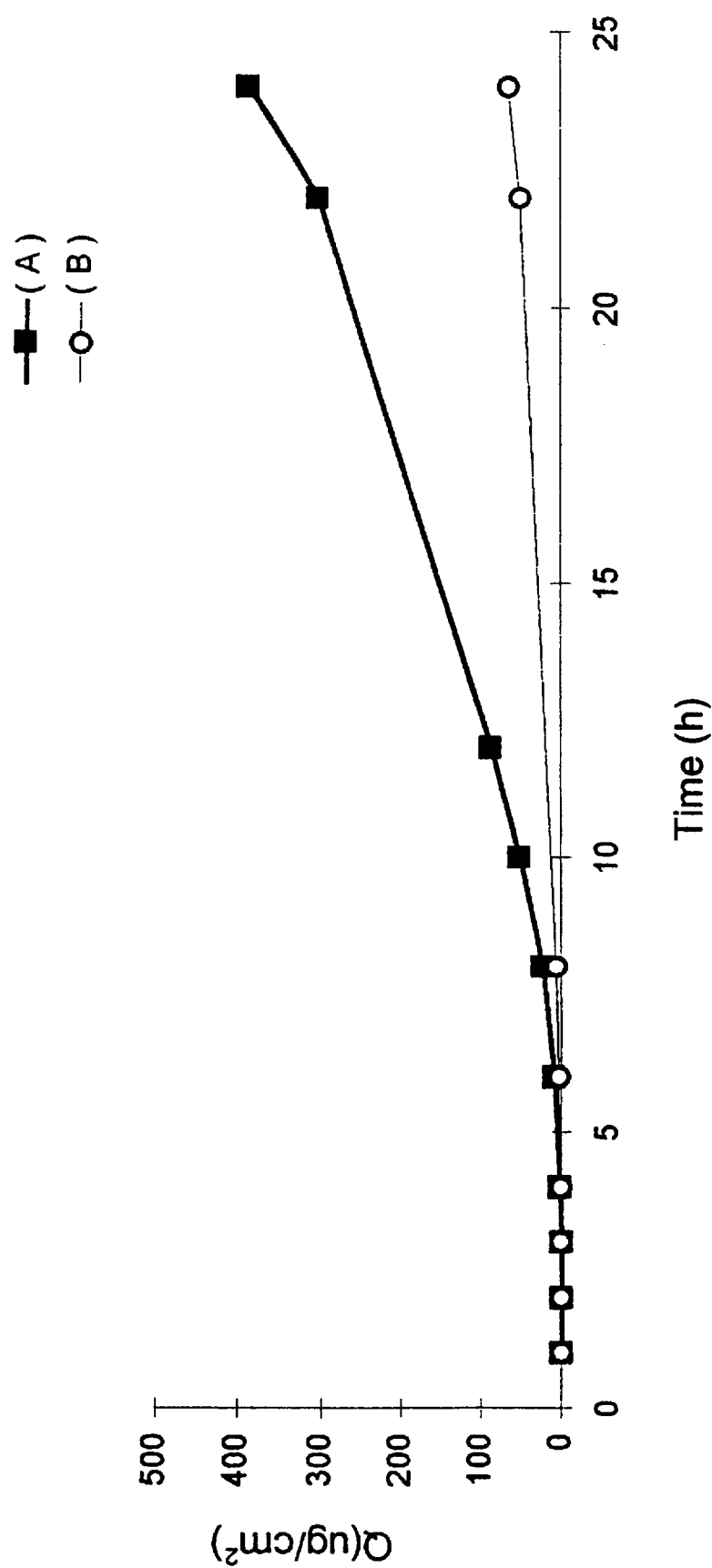
FIG. 5 represents the transdermal permeation of hydroxyethyl pyrrolidone diclofenac in the formulation I of example 1 (curve (A)) in comparison with formulation A of the example 7 (curve (B)).
Figure 6:
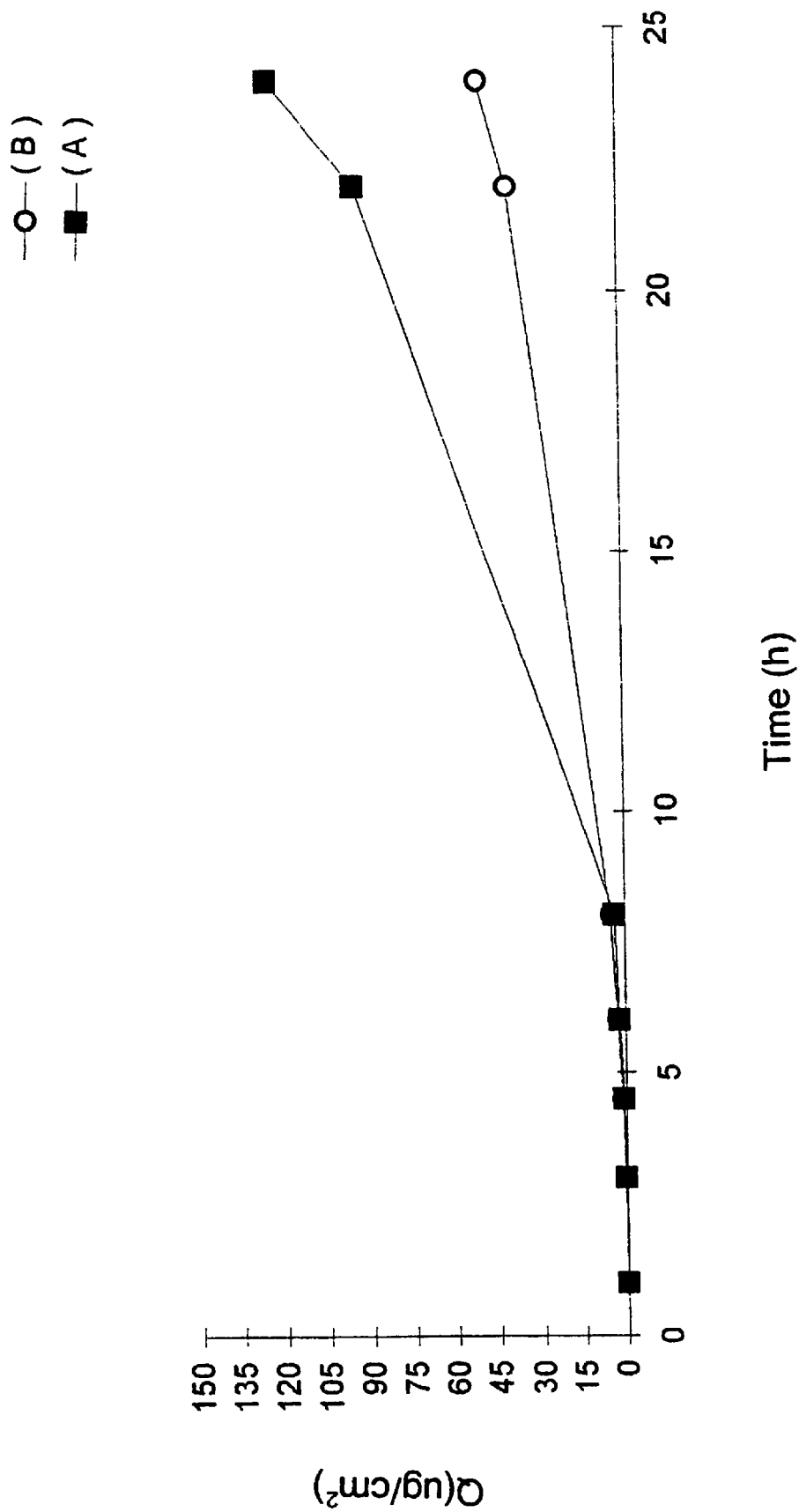
FIG. 6 represents the transdermal permeation of sodium diclofenac in the formulation V of the example 1 (curve (A)) in comparison with the formulation B of the example 7 (curve (B)).
Figure 7:
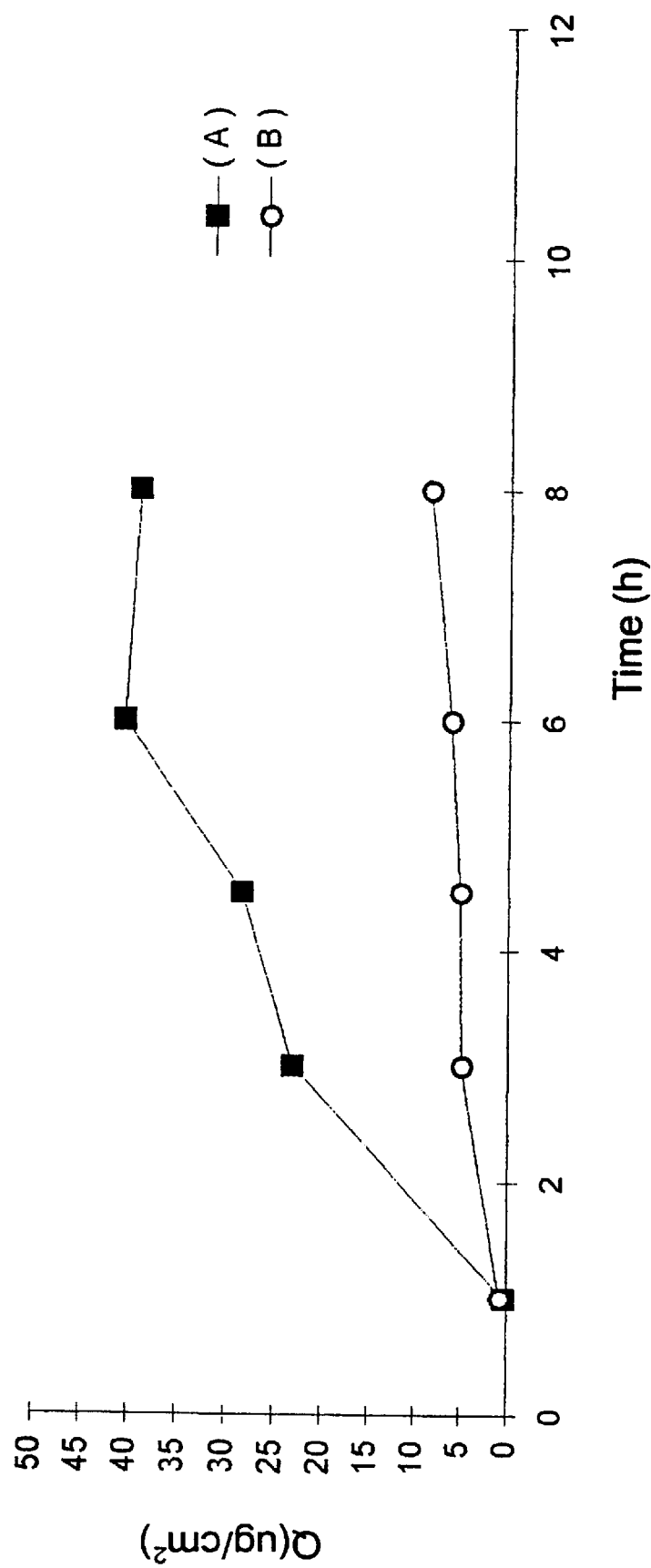
FIG. 7 represents the transdermal permeation of the papaverin HCl in the formulation XII of the example 1 (curve (A)) in comparison with formulation C of the example 7 (curve (B)).
Figure 8:
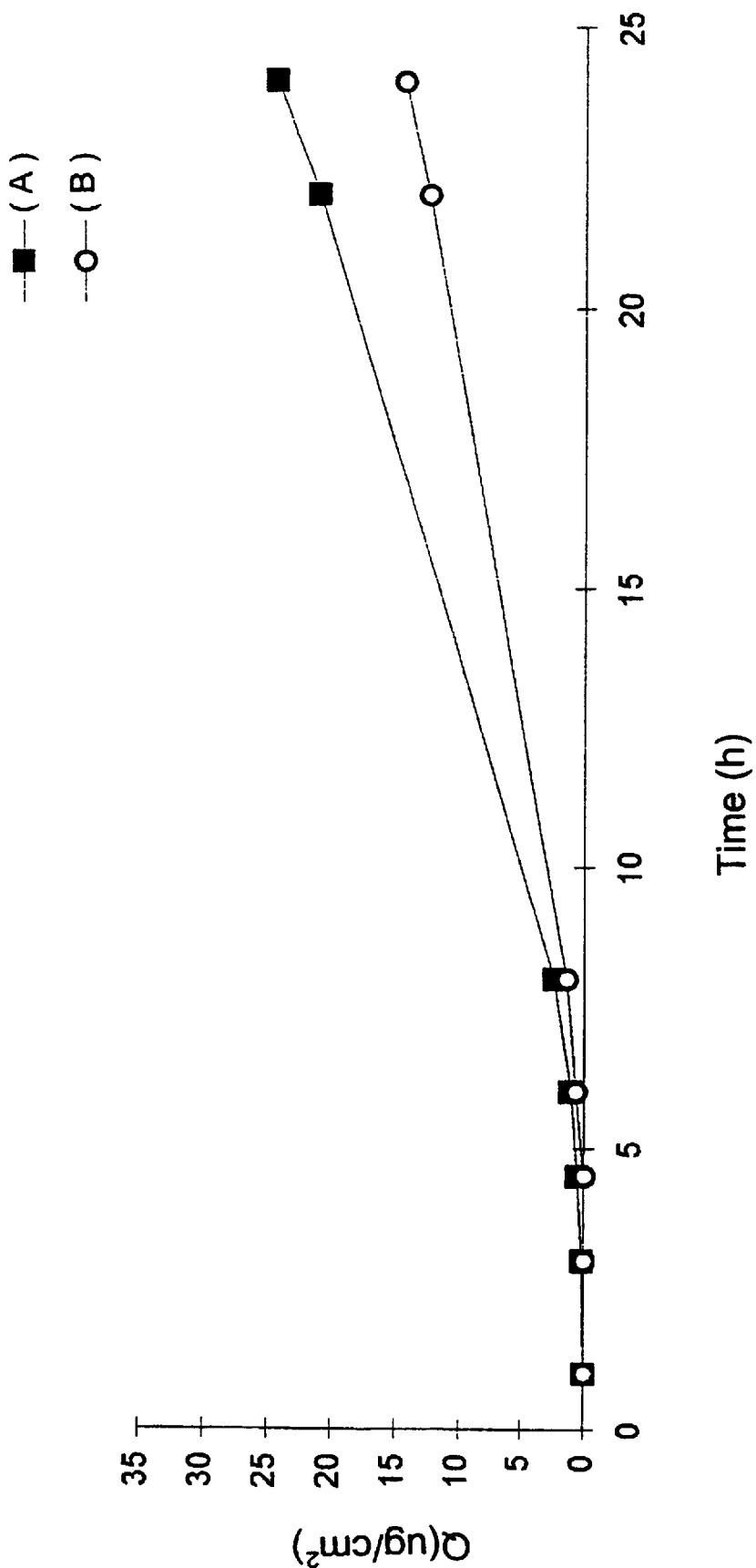
FIG. 8 represents the transdermal permeation of nimesulide according to the formulation XIV of the example 1 (curve (A)) in comparison with the formulation D of the example 7 (curve (B)).
Figure 9:
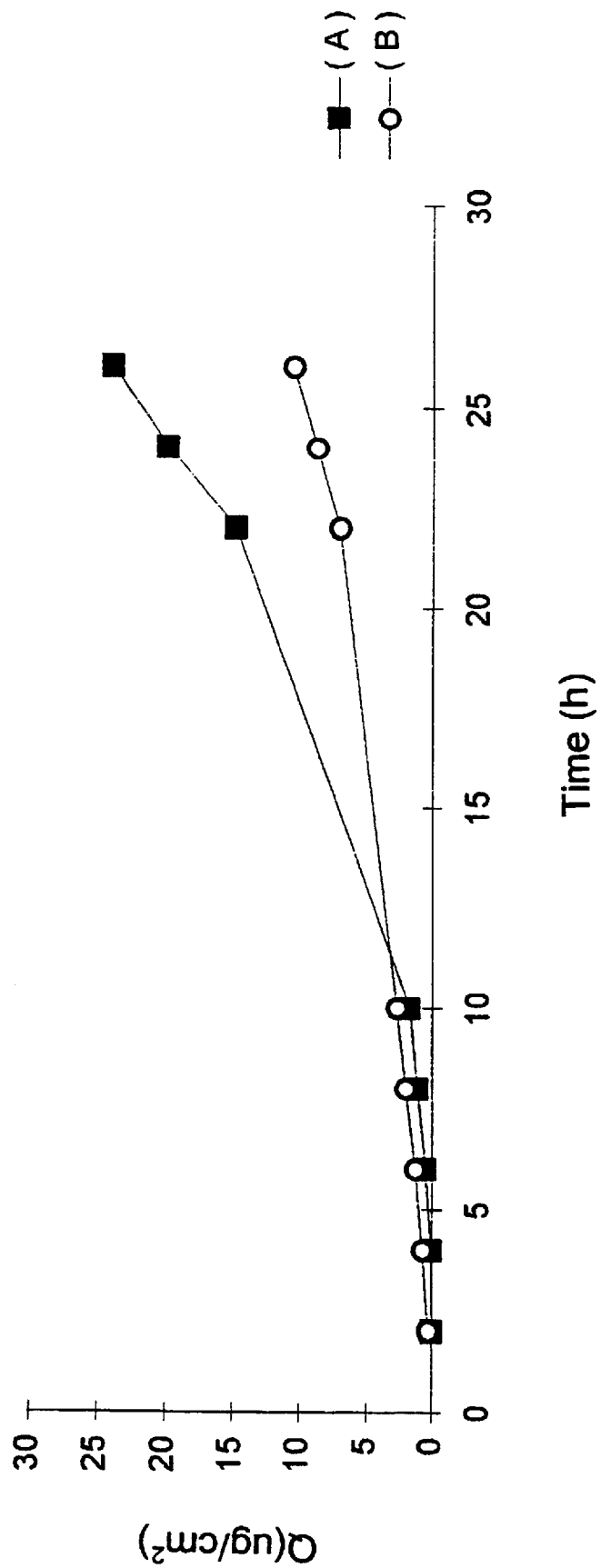
FIG. 9 represents the transdermal permeation of acyclovir of the formulation XVI of the example 1 (curve (A)) in comparison with the formulation E of the example 7 (curve (B)).

In particular, FIG. 5 shows the transdermal permeation of diclofenac hydroxyethylpyrrolidine in the composition I of example 1 (curve (A)), compared with the composition A, of example 7 (curve (B));

FIG. 6 shows the transdermal permeation of sodium diclofenac in the composition V of example 1 (curve (A)), compared with the composition B of example 7 (curve (B));

FIG. 7 shows the transdermal permeation of papaverine-.HCl in the composition XII of example 1 (curve (A)), compared with the composition C of example 7 (curve (B));

FIG. 8 shows the transdermal permeation of nimesulide according to the composition XIV of example 1 (curve (A)), compared with the composition D of example 7 (curve (B));

FIG. 9 shows the transdermal permeation of acyclovir according to the composition XIV of example 1 (curve (A)), compared with the composition E of example 7 (curve (B)).

The reported results elicit a substantial increase of transdermal permeation of the active principles, when formulated according to the invention.

Figure 10:
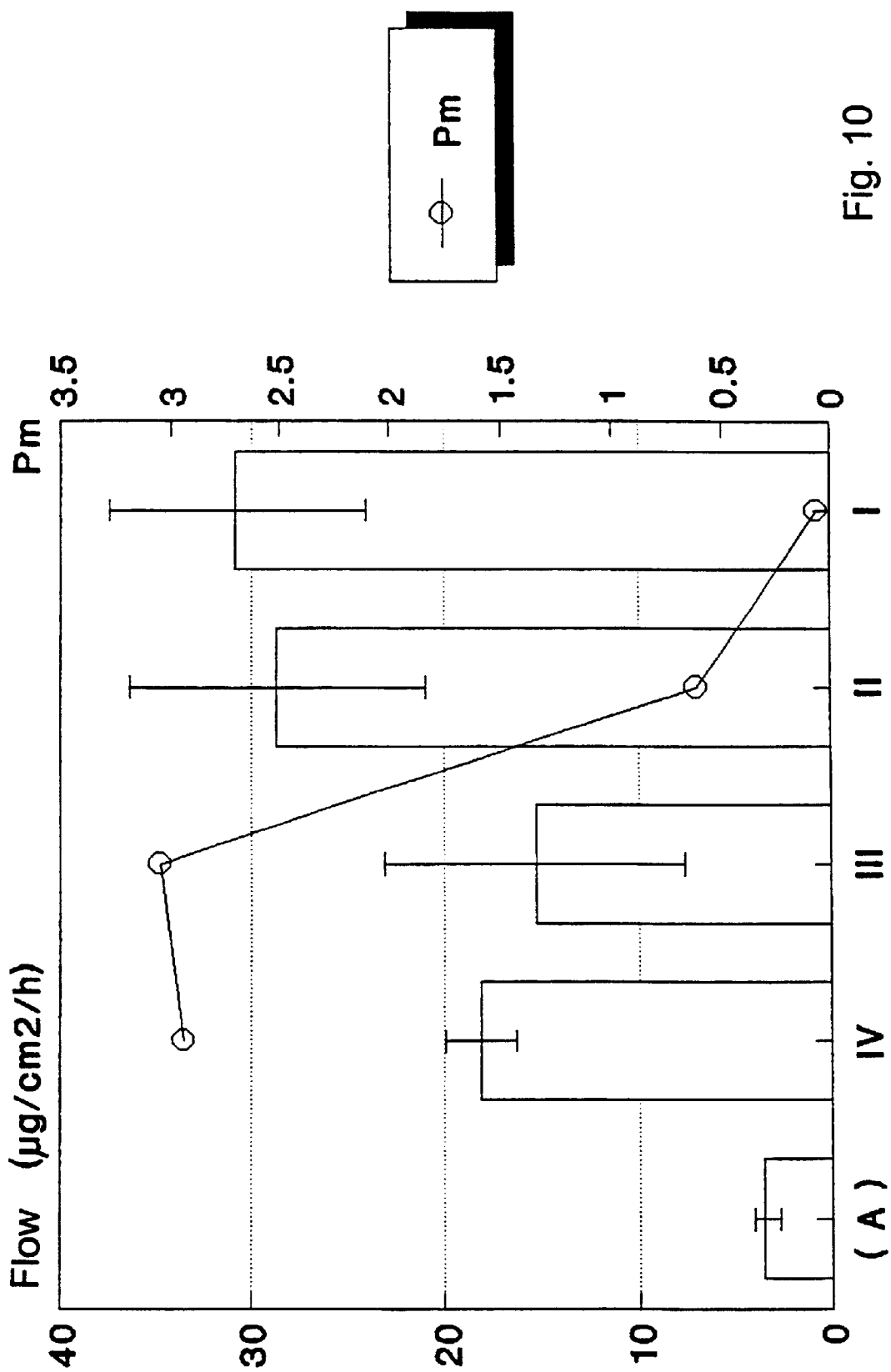
FIG. 10 represents the transdermal permeation rate (flow) and the partition factors ($P_m$) of hydroxyethyl pyrrolidine diclofenac (DIEP) of the formulations I, II, III and IV of the example 1 containing N-methyl pyrrolidone (NMP) in comparison with the formulation (A) without NMP.
Figure 11:
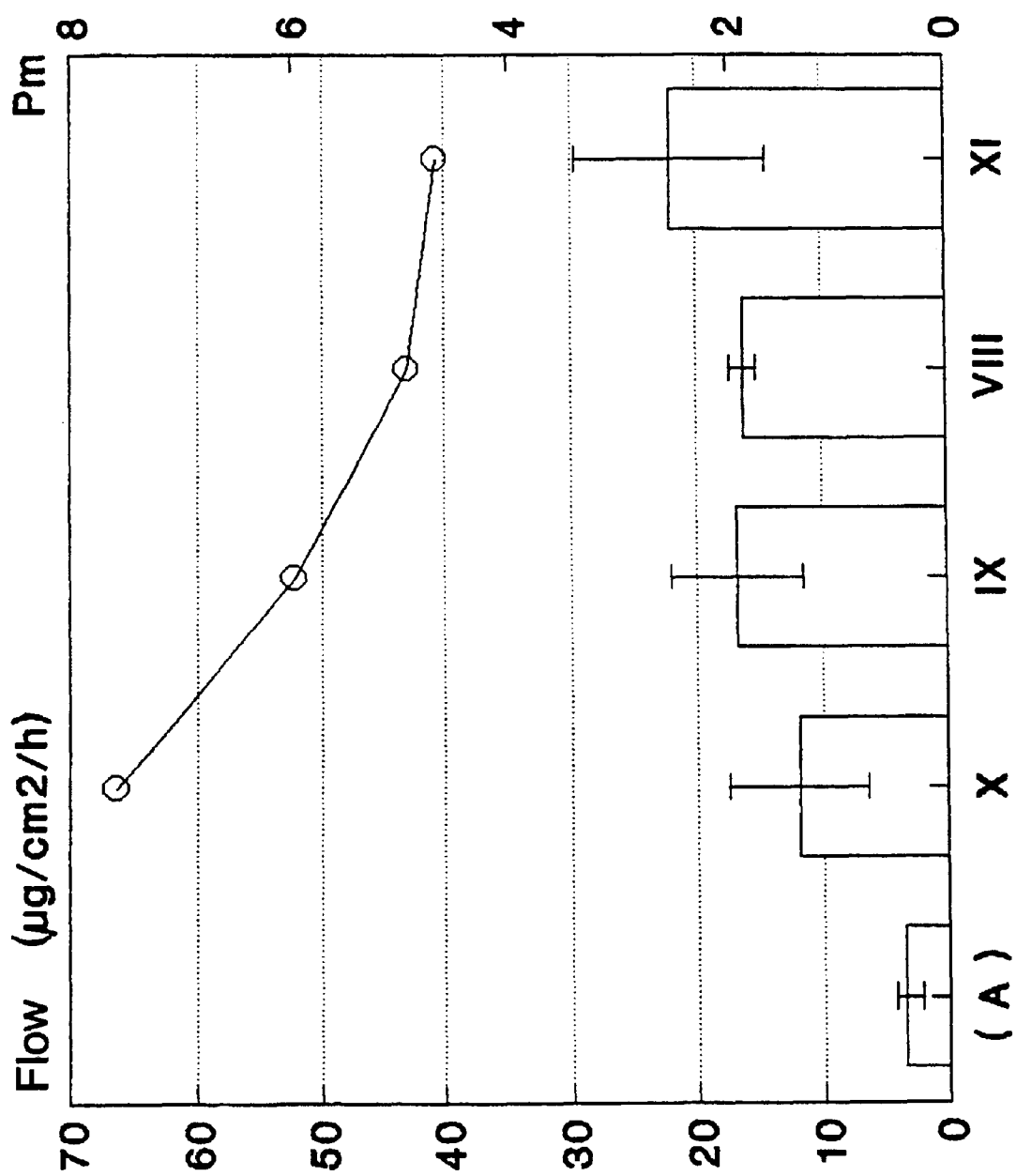
FIG. 11 represents the transdermal permeation rate (flow) and the partition factors ($P_m$) of (DIEP) of the formulations VIII, IX, x and XI of the example 1 containing propylene glycol (PG) in comparison with the formulation (A) without PG.

Furthermore, we compared the transdermal flux values for one active principle (DIEP) as well as for two "partition modifiers" (N-methylpyrrolidone, NMP; propylene glycol, PG) in different compositions, and the partition coefficient values ($P_m$) of the active principle in the aqueous and oil phases of the compositions. Comparative diagrams are shown for the compositions containing DIEP and NMP (FIG. 10) and DIEP and PG (FIG. 11). FIG. 10 shows the transdermal permeation rate (flux) and the partition coefficient ($P_m$) of diclofenac hydroxyethylpyrrolidine (DIEP) relevant to the compositions I, II, II, IV of example 1 containing the partition modifier N-methylpyrrolidone (NMP), in comparison with the composition (A) lacking NMP.

FIG. 11 shows the transdermal permeation rate (flux) and the partition coefficient ($P_m$) of DIEP relevant to the compositions VII, IX, X, XI of example 1 containing the partition modifier propylene glycol (PG), in comparison with the composition (A) lacking PG.

These diagrams make evident that the unexpected modification of the active principle distribution among the oily phase ("reservoir") and the aqueous phase ("enhancer") of the compositions of the invention, caused by the "partition modifiers", affects greatly and unexpectedly the transdermal permeation rate of the active principles.

What is claimed is:

1. A process for the preparation of a biphasic multicomponent pharmaceutical composition consisting of an oil phase and a water phase wherein the composition comprises:

one or more lipophilic or oil carrier;

one or more hydrophilic or aqueous carrier;

one or more ionic or nonionic surfactant;

one or more cosurfactant; and one or more active principle for pharmaceutical use, wherein said composition further comprises a compound able to modify the partition of the active principle between said phases, selected from the group consisting of N-methyl pyrrolidone (NMP), β-cyclodextrin, hydroxypropyl β-cyclodextrin and dimethyl β-cyclodextrin, the preparation process comprising the following steps:

a) maintaining a mixture consisting of the lipophilic or oil carrier, the cosurfactant and a fraction of the surfactant under mild stirring and temperature control;

b) adding the hydrophilic or aqueous carrier to the mixture of step a) while maintaining the mild stirring and the temperature control;

c) adding the compound able to modify the partition of the active principle to one of the two phases before the mixing, according to its miscibility with the aqueous or oil phase;

d) adding the residual fraction of surfactant;

e) adding the active principle, in dissolved and/or dispersed form, to the composition already constituted.

2. The process according to claim 1 wherein the temperature of steps a) and b) is between 5 and 85° C.

3. The composition according to claim 1 wherein the composition is further formulated into systems for transdermal use in form of matrix systems, reservoir systems, multilayer systems and drug- in-adhesive systems.

4. The composition according to claim 1 wherein the composition is further formulated in systems for oral or transmucosal use in form of liquid capsules, soft-gel capsules, suppositories and applicators.

5. A process for the preparation of a biphasic multicomponent pharmaceutical composition consisting of an oil phase and a water phase, comprising:

one or more lipophilic or oil carrier having a wet percentage of between 0.5 to 80%;

one or more hydrophilic or aqueous carrier having a weight percentage of between 0.5 to 70%;

one or more ionic or nonionic surfactant having a weight percentage of between 0.1 to 50%;

one or more cosurfactant having a weight percentage of between 0 and 50%; and one or more active principle for pharmaceutical use having a weight percentage of between 0.1 to 60%, wherein said composition further comprises a compound able to modify the partition of the active principle between said phase having a weight percentage of between 0.1 to 30%, selected from the group consisting of N-methyl pyrrolidone (NMP), β-cyclodextrin, hydroxypropyl β-cyclodextrin and dimethyl β-cyclodextrin, comprising the following steps:

a) maintaining a mixture consisting of the lipophilic or oil carrier, the cosurfactant and a fraction of the surfactant under mild stirring and temperature control;

b) adding the hydrophilic or aqueous carrier to the mixture of step a) while maintaining the mild stirring and the temperature control;

c) adding the compound able to modify the partition of the active principle to one of the two phases before the mixing, according to its miscibility with the aqueous or oil phase;

d) adding the residual fraction of surfactant;

e) adding the active principle, in dissolved and/or dispersed form, to the composition already constituted.

6. The process according to claim 5 wherein the temperature of steps a) and b) is between 5 and 85° C.

7. The process according to claim 5 wherein the composition is further formulated into systems for transdermal use in form of matrix systems, reservoir systems, multilayer systems and drug- in-adhesive systems.

8. The process according to claim 5 wherein the composition is further formulated in systems for oral or transmucosal use in form of liquid capsules, soft-gel capsules, suppositories and appllicators.

* * * * *

UNITED STATES PATENT AND TRADEMARK OFFICE
CERTIFICATE OF CORRECTION

PATENT NO. : 6,495,160 B2
DATED : December 17, 2002
INVENTOR(S) : Pierandrea Esposito et al.

It is certified that error appears in the above-identified patent and that said Letters Patent is hereby corrected as shown below:

Column 19,
Line 14, after the word "a" the word "wet" should be -- weight --.
Line 27, "the word "phase" should be -- phases --.

Column 20,
Line 27, the word "appllicators" should be -- applicators --.

Signed and Sealed this

Twenty-fourth Day of June, 2003

JAMES E. ROGAN
*Director of the United States Patent and Trademark Office*